US011433195B2

(12) United States Patent
Steinberg

(10) Patent No.: US 11,433,195 B2
(45) Date of Patent: Sep. 6, 2022

(54) BREATHING DEVICE AND METHOD OF CONTROLLING BREATHING USING THE DEVICE

(71) Applicant: Todd Joseph Steinberg, Fort Lauderdale, FL (US)

(72) Inventor: Todd Joseph Steinberg, Fort Lauderdale, FL (US)

( * ) Notice: Subject to any disclaimer, the term of this patent is extended or adjusted under 35 U.S.C. 154(b) by 114 days.

(21) Appl. No.: 15/685,242

(22) Filed: Aug. 24, 2017

(65) Prior Publication Data
US 2018/0056017 A1  Mar. 1, 2018

Related U.S. Application Data

(60) Provisional application No. 62/379,533, filed on Aug. 25, 2016.

(51) Int. Cl.
*A61M 21/02* (2006.01)
*A61M 16/00* (2006.01)
*A61M 16/08* (2006.01)

(52) U.S. Cl.
CPC .... *A61M 16/0045* (2013.01); *A61M 16/0866* (2014.02); *A61M 21/02* (2013.01); *A61M 16/0003* (2014.02); *A61M 2202/02* (2013.01); *A61M 2209/088* (2013.01)

(58) Field of Classification Search
CPC .......... A61M 16/0045; A61M 16/0003; A61M 2202/02; A61M 16/0488; A61M 16/049; A61M 21/02; B65D 23/108; B65D 25/32
See application file for complete search history.

(56) References Cited

U.S. PATENT DOCUMENTS

| 515,637 | A | * | 2/1894 | Wilhide | A63B 23/18 482/13 |
| 2,499,855 | A | * | 3/1950 | Gamble | G10D 9/02 84/383 R |
| 3,565,071 | A | * | 2/1971 | Cobb | A61M 15/00 128/203.24 |
| 4,054,134 | A | * | 10/1977 | Kritzer | A61M 16/00 128/205.24 |
| 4,167,946 | A | * | 9/1979 | Sandstrom | A61M 25/02 128/207.17 |
| 4,221,381 | A | * | 9/1980 | Ericson | A63B 23/18 482/13 |
| 4,533,137 | A | * | 8/1985 | Sonne | A63B 23/18 128/207.16 |
| 4,770,413 | A | * | 9/1988 | Green | A63B 23/18 137/269.5 |

(Continued)

*Primary Examiner* — Samchuan C Yao
*Assistant Examiner* — Nathan M Le
(74) *Attorney, Agent, or Firm* — Jeffrey S. Melcher; Melcher Patent Law PLLC

(57) ABSTRACT

A breathing device having an elongated body which may be cylindrical in shape. The body can be hollow so as to form the general shape of a tube. The tube has an opening and an exit. The user may interact with the device by placing their mouth in communication with the opening so that the user may exhale through their mouth into and through the hollow body of the device. The exit can comprise a connective part which may be configured to be coupled to one or more objects such as clothing, strings, necklaces and chains, bracelets, headbands and hair accessories, and the like.

21 Claims, 6 Drawing Sheets

(56) References Cited

U.S. PATENT DOCUMENTS

Figure 1:
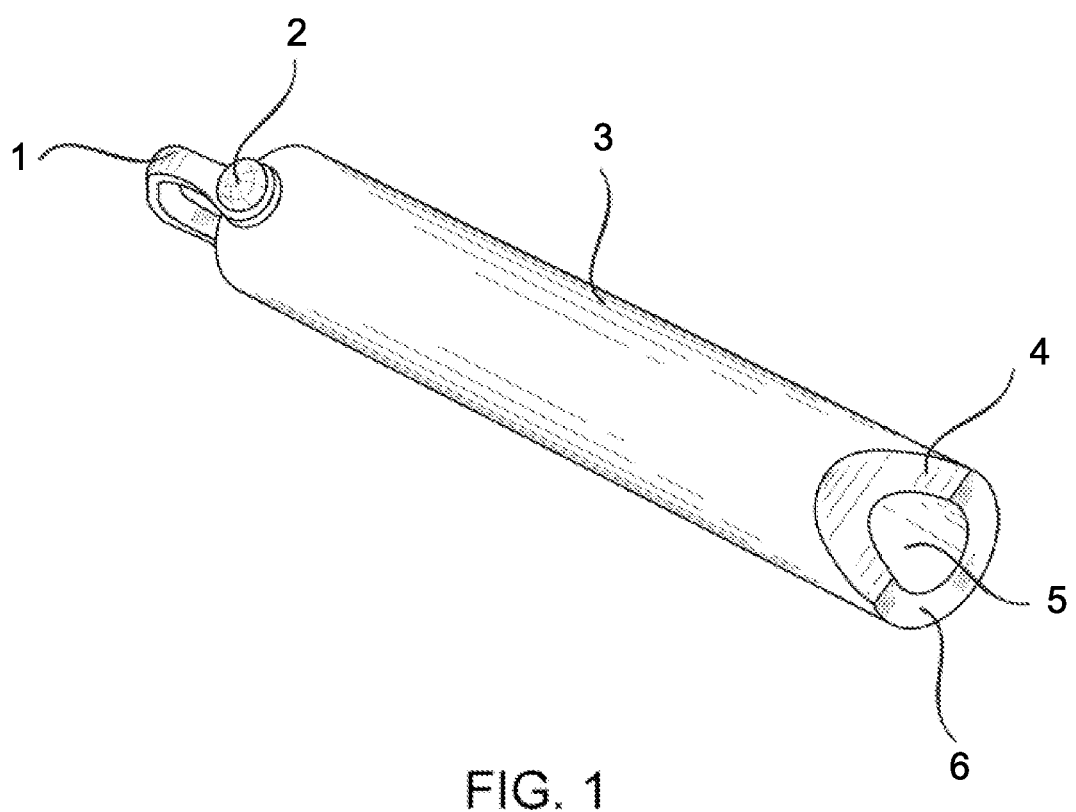

| | | | | |
|---|---|---|---|---|
| 4,973,047 A * | 11/1990 | Norell | A63B 23/18 | 482/13 |
| 4,995,384 A * | 2/1991 | Keeling | A61M 16/0672 | 128/204.18 |
| 5,018,517 A * | 5/1991 | Liardet | A63B 23/18 | 128/200.24 |
| 5,165,393 A * | 11/1992 | Kawaguchi | A63B 23/18 | 128/200.24 |
| 5,193,529 A * | 3/1993 | Labaere | A63B 23/18 | 128/200.24 |
| 5,357,837 A * | 10/1994 | Disera | G10D 9/023 | 84/383 R |
| 5,658,221 A * | 8/1997 | Hougen | A63B 23/18 | 482/13 |
| 5,890,998 A * | 4/1999 | Hougen | A61M 16/0006 | 482/13 |
| 5,899,832 A * | 5/1999 | Hougen | A63B 23/18 | 128/200.24 |
| 6,083,141 A * | 7/2000 | Hougen | A61M 16/0006 | 128/202.16 |
| 6,942,362 B1 * | 9/2005 | Deutsch | B60Q 1/326 | 362/116 |
| 8,382,644 B1 * | 2/2013 | Suprun | A63B 21/008 | 128/200.24 |
| 2006/0081241 A1 * | 4/2006 | Quinn | A61M 16/049 | 128/200.24 |
| 2006/0144398 A1 * | 7/2006 | Doshi | A61M 16/20 | 128/204.23 |
| 2007/0089740 A1 * | 4/2007 | Baumert | A61M 16/0488 | 128/203.12 |
| 2008/0251069 A1 * | 10/2008 | Cegla | A63B 21/00069 | 128/200.24 |
| 2010/0085738 A1 * | 4/2010 | Bertken | F21L 4/02 | 362/157 |
| 2011/0146672 A1 * | 6/2011 | Schmal | A63B 23/18 | 128/200.24 |
| 2015/0209541 A1 * | 7/2015 | Harwood | A61M 16/0605 | 128/205.25 |
| 2015/0224270 A1 * | 8/2015 | Frandson | A61M 16/0003 | 128/204.18 |
| 2016/0375213 A1 * | 12/2016 | Zlupko | A61M 16/0488 | 128/200.24 |

\* cited by examiner

BREATHING DEVICE AND METHOD OF CONTROLLING BREATHING USING THE DEVICE

This application claims priority to U.S. Provisional Patent Application Ser. No. 62/379,533, filed 25 Aug. 2016, the complete disclosure of which is incorporated herein by reference.

FIELD OF THE INVENTION

The invention relates a breathing device and a method of using the breathing device to control breathing.

BACKGROUND OF THE INVENTION

Stress represents one of the biggest barriers to happiness. Anxiety Disorders affect 18.1 percent of adults in the United States (approximately 40 million adults between the ages of 18 to 54). People have an average of 40,000 thoughts per day and don't know how to manage anxieties ranging from personal relationships, work, school, parenting, money, health, and more.

The proliferation of digital technology is perpetuating stress and anxiety because of a developing co-dependence on electronic devices which crowds the mind. A solution to help counter the growing pandemic of stress is by rechanneling our breath.

70% of the toxins inside of your body are removed through the lungs. When we're stressed, our breath is typically shallow or held which increases heart rate and/or blood pressure. Breath is the key to physical and mental well-being and can boost energy, and relieve pain. To maintain peak health, our cells must be oxygenated through correct breathing. We've been commonly instructed to take deep breaths as a practice in order to combat stress and feel calm. The problem is that most people are not now aware of how their breath affects their state of mind and don't know how long to inhale or exhale in order to reap the real benefits of deep breathing. Longer inhalations can activate higher tension while longer exhalations do the opposite.

The ancient practices of meditation and yoga can be used to refocus our breath in order to bring us back to the present moment which coupled with other techniques can lead to peace of mind. Unfortunately, meditation and yoga have been difficult for people to learn because there are no physical tools to serve as a preliminary learning resource. There are classes, online tutorials, videos, and books but no tangible accessory to physically help guide breathe and remind them to be calm.

SUMMARY OF THE INVENTION

An objective of the invention is to provide a device and method for controlling breathing.

In preferred embodiments, the breathing tube device comprises a tool engineered to deliver the proper exhalations necessary to calm the body and mind and is the first of its kind. By exhaling through the device, a user's breath is intentionally lengthened to slow the rhythm of breathing. The device is also designed as a jewelry accessory to be worn or carried as a reminder to be still or calm. In some embodiments, the breathing tube device can comprise an elongated body which may be cylindrical in shape. The body can be hollow so as to form the general shape of a tube. The tube can comprise a first end (bottom) and a second end (top). The user may interact with the device by placing their mouth in communication with the first end so that the user can exhale through their mouth into and through the hollow body (chamber) of the device. In further embodiments, the second end can comprise a connective part (such as a bail) which can be configured to be coupled to one or more objects such as clothing, strings, necklaces and chains, bracelets, headbands and hair accessories, and the like.

Slowing the rhythm of breath by exhaling through the tube, the user should experience a physiological and neurological shift to calm and stillness. The purpose of guided breathe is to feel more content and present in every moment, consistent with meditation which is defined as to engage in mental exercise (as concentration on one's breathing or repetition of a mantra) for the purpose of reaching a heightened level of spiritual awareness.

The guided breathe technique through the device can serve as a preventative measure to initiate proper breathe to start one's day with peace of mind or as a rescue breathe to help calm anxious thoughts.

BRIEF DESCRIPTION ON THE DRAWINGS

Figure 2:
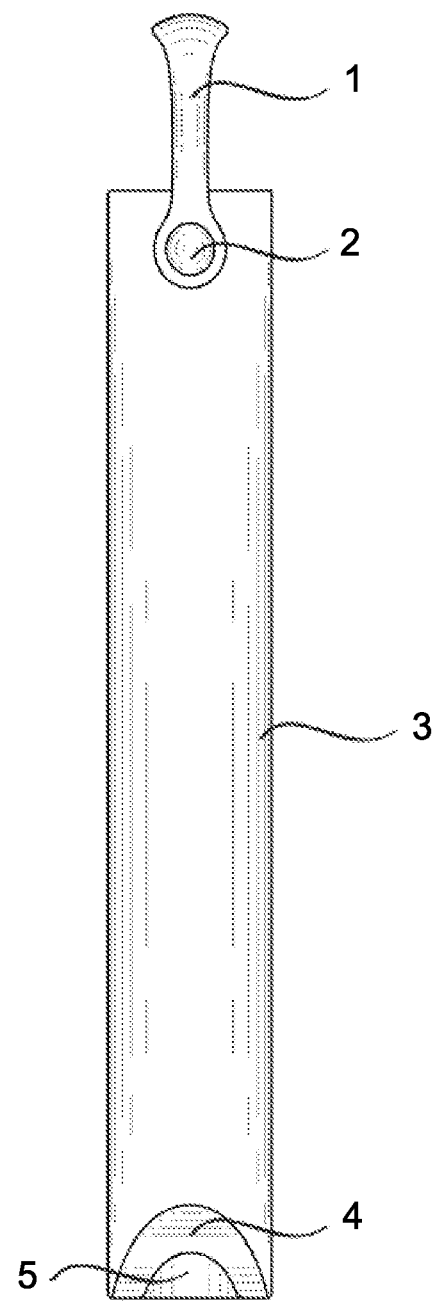
Figure 3:
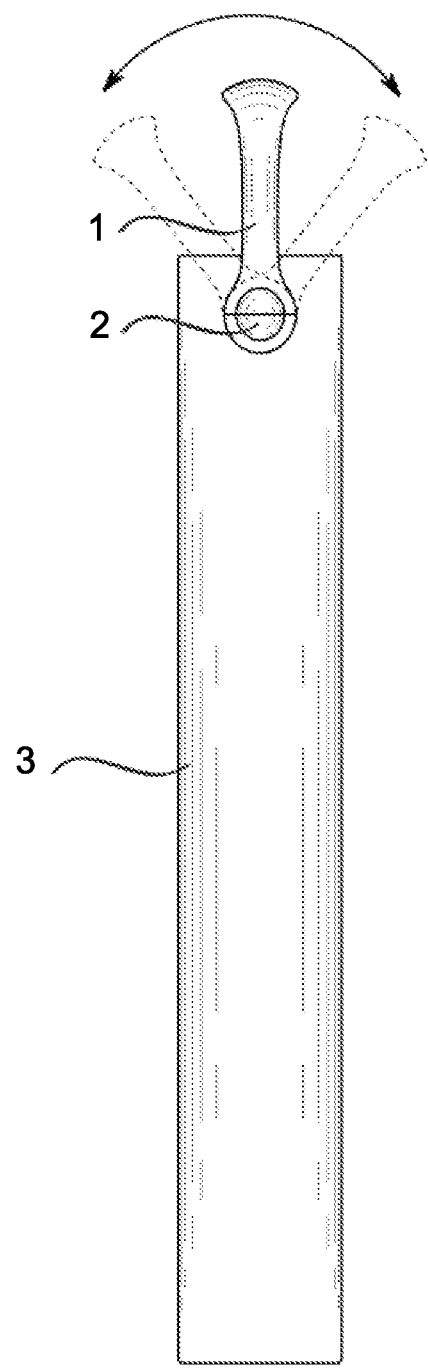
Figure 4:
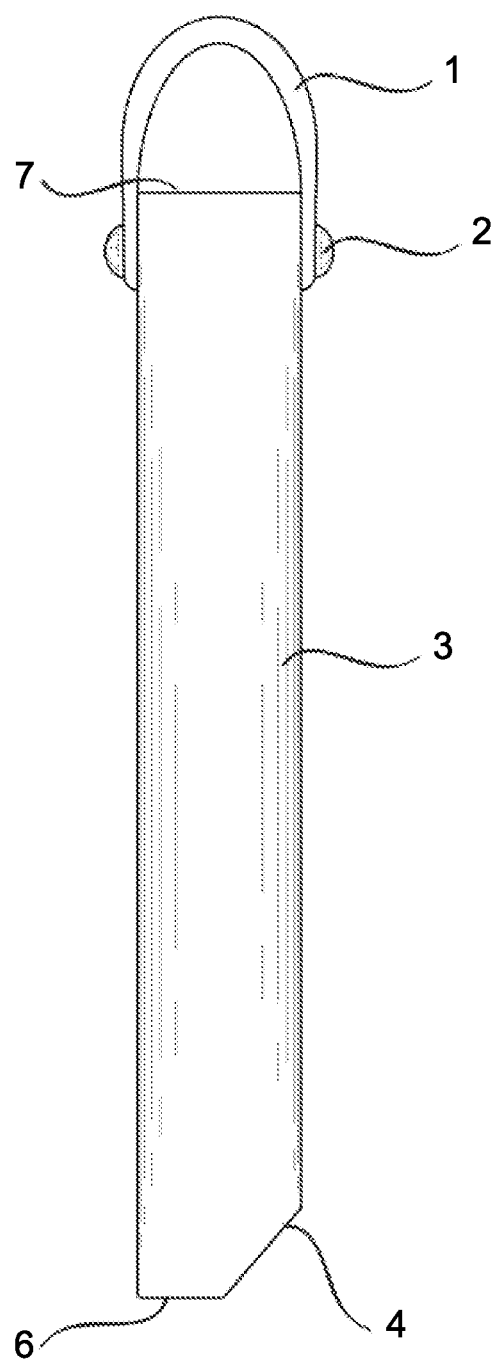
Figure 5:
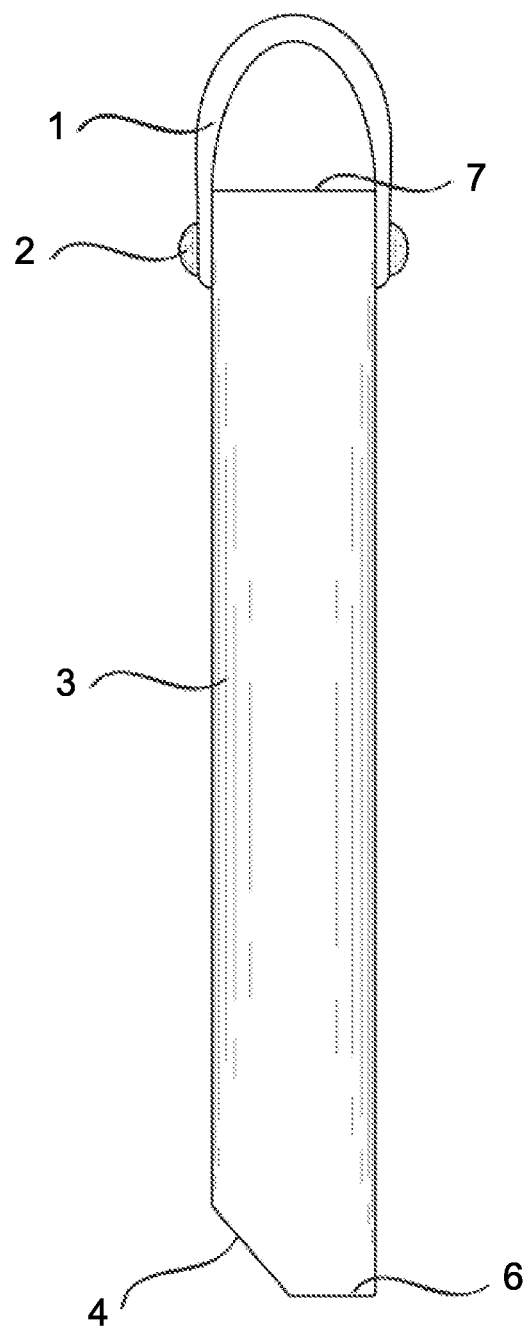
Figure 6:
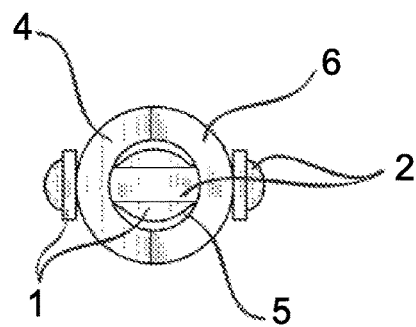
Figure 7:
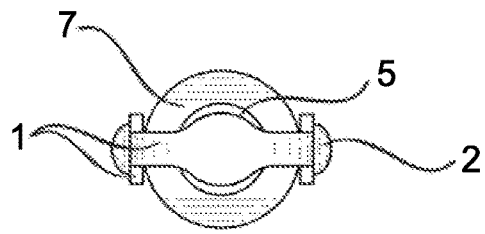
Figure 8:
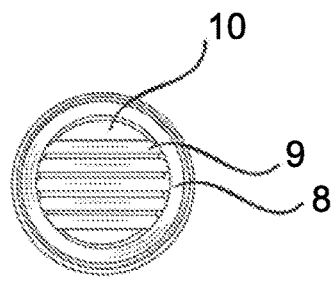
Figure 9:
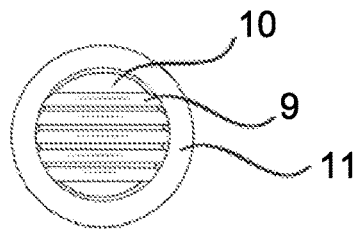
Figure 10:

FIG. 1 shows a perspective view of a breathing device.
FIG. 2 illustrates a front view of a breathing device.
FIG. 3 illustrates a back view of a breathing device.
FIG. 4 illustrates a right side view of a breathing device.
FIG. 5 illustrates a left side view of a breathing device.
FIG. 6 illustrates a bottom view of a breathing device.
FIG. 7 illustrates a top view of a breathing device.
FIGS. 8-10 illustrate an exit cap for adjusting air flow.

DETAILED DESCRIPTION OF THE INVENTION

The invention will be explained with reference to the attached non-limiting FIGS. 1-7.

The example of the breathing device shown in the Figs. comprises an optional bail 1 attached to the breathing tube 3 by a pin 2. The purpose of the bail 1 is to connect the breathing tube 3 to a securing structure, such as a chain or cord so that the tube 3 can be worn as a necklace. The bail 1 can also connect to other accessories like a key chain or bracelet as desired. The bail 1 can also swivel on an axis about the pin 2 as show in FIG. 3 if the user desires to move the position of the bail 1 in relation to the breathing tube 3. This bail is preferably not removable. The pin 2 attaches the bail 1 to the breathing tube 2 by serving as an axis. The pin 2 can penetrate both sides of the breathing tube 2 to harness the bail 1. The pin 2 is preferably not removable.

The breathing tube 3 has an elongated shape with an opening 6 at the bottom end and an exit 7 at a top end and a chamber 5 that travels a length of the tube 3. The tube 4 and chamber 5 each preferably have a generally round shape. However, the term "tube" is not limited to a round shape, but, can include any desired shape as desired, such as oval, square, polygonal, irregular, etc. The length of the breathing tube 3 in the produced example was 50.8 millimeters (not including the bail 1). The length of the tube 3 can be any desired length, such as from 20-152 millimeters, preferably from 30-75 millimeters.

The breathing tube 3 can have an angled edge 4 at the bottom. The purpose of this angled edge 4 is for the user to place their lips against when breathing through the tube 3. The surface of the angled edge 4 can be flat.

The opening 6 (aperture), the exit 7, and the chamber 5 can each be separately sized to provide a desired resistance to exhaling of the user's breath during use of the tube. For example, a larger size opening 6, exit 7, and/or chamber 5 can be used for a larger user, and a smaller size opening 6, exit 7 and/or chamber 5 can be used for a smaller user. A diameter of the opening 6, exit 7 and chamber 5 in a produced example was 4.76 millimeters, which was universal from top to bottom of the breathing tube 3. Examples of suitable diameters for the opening 6, chamber 5 and exit 7 are from 2-10 millimeters, preferably from 3-6 millimeters. The user can cover their lips around the tube opening 6 at the bottom of the breathing tube and exhale through the tube opening which then exits through the opposite side at exit 7.

The breathing tube device was invented and engineered to perform one or more of the following benefits:

Stress Combatant: reduces anxiety and stress to increase happiness.

Meditational/Yoga Learning Tool: Introduces and teaches breathing aspects of meditation and Yoga.

Reminder to be mindful and product inspiration.

Fashionable Accessory: wear symbol to represent a lifestyle committed to stillness.

Yoga Accessory: assists in breathing to support the practice

Stress Combatant: When confronted with anxiety and stress from external or internal sources, the nervous system reacts by creating physical responses which include increased heart rate, blood pressure, muscular tension, and breathing rhythm. These responses can cause anxiety, insomnia, irritability, mood swings, and depression, interfere with communication, reduce productivity, and increase risk for heart disease.

Having stressful thoughts makes our bodies tighter and tenser by inhaling longer than we're exhaling. The two branches of the autonomic nervous system regulate the heart, lungs, circulatory system, and glands. In a sense, they work in opposition to each other: the sympathetic system helps the body gear up for physical activity by accelerating the heart rate, raising blood pressure, and increasing tension in the large skeletal muscles; the parasympathetic system does the opposite—decreasing heart rate, lowering blood pressure, and releasing muscular tension. Inhalation stimulates the sympathetic system, and exhalation stimulates the parasympathetic system. When we are under pressure, thinking stressful thoughts, we make our bodies tighter and tenser by inhaling longer than we're exhaling.

The body is equipped with a natural breathing function to reduce the severity of these effects and in some cases, reverse their course. When the parasympathetic nervous system is activated to initiate deeper and more meaningful exhalations, heart rate, blood pressure, and muscular tension each lower which allows the body to enter a more still and relaxed state. Emphasizing the exhalation also discharges volatile toxins and carbon dioxide from the lungs, leaving a vacuum that will be filled with fresh air when you inhale. The breathing tube does not cure and is not intended to replace what a healthcare provider has advised patients for stress.

The breathing tube device is configured to provide people with a physical tool engineered to produce these longer and more meaningful exhalations in order to achieve a more relaxed state in the event they need or want it. The user can take as many breaths through the device as they prefer until they reach their ideal state of mind or physicality which typically can range from 10 seconds to 2 minutes. The device intentionally resets the pace of breath of a user by extending the exhalation which can reset the user's state of mind and reverse the negative effects of stress or simply prevent stress by committing to a calm pace of breath and calm state of mind before a stressful situation.

An example of when someone might use the breathing tube would be if they are confronted with a stressful situation like sitting in traffic. The user notices an increase in dissatisfaction with their environment and is restless, annoyed, irritated, or angry. The user would simply reach for the breathing tube accessory, deeply inhale through their nose and exhale through the device until their state of mind reaches a calmer or more comfortable place.

Another example scenario would be if the user is anxious about entering an important meeting at work and needs to be calm in order to focus. The user could simply exhale through the breathing tube device until the anxiety or increased heart rate abates and they feel more equipped to focus because they've reached a relaxed and calm place in their mind. The pace of breathing also reminds the user to commit to that pace in order to stay calm.

The breathing tube can also be demonstrated by someone using the device prior to feeling stress as a means to prevent anxiety or discomfort. For instance, someone can exhale through the device in the morning before they go to work in order to start their day mindfully, intentionally committing to being present and pacing their breath.

The resulting absence of stress and anxiety leads to a happier state of being. Merrium-Webster defines happiness as a state of well-being and contentment, joy, a pleasurable or satisfying experience. The breathing tube device intentionally aids the user to a happier state by aligning mind and body with peace through more conscious and valuable breathes.

Meditational Learning Tool: The term meditation refers to a broad variety of practices that includes techniques designed to promote relaxation, build internal energy or life force and develop compassion, love, patience, generosity, and forgiveness. One of these practices centers on breath as the passage to peace of mind. By focusing on the breath, a user becomes aware of the mind's tendency to jump from one thing to another. The discipline of concentration brings the user back to the present moment and ultimately a still place. When done correctly, proper breathing eliminates wastes from the lungs while calming and nurturing the nervous system. It's an effective way to prepare the body, breath, and mind for meditation.

Frustration can develop when someone who is trying to learn meditation cannot grasp one of the first steps which is proper pace of breath. This frustration can prevent the beginner from progressing to the next stages which open the mind to peace, awareness, and presence. The breathing tube removes the frustration of pacing one's breath because the user can use a physical tool (like training wheels on a bicycle) instead of trying to independently breathe deeply enough to reach optimal levels. The simple act of focusing on the breathing tube will turn the user's attention specifically to their breath and away from other distractions. When the mind begins to wander, the user can return to their breath because the tube provides them with a physical tool to keep focused and present. Instead of being worried about breathing the wrong way, the user will feel confident and less distracted. The next steps of meditating are centered on getting to know the mind while developing a better awareness of life, love, energy, kindness, and light.

According to the Mayo Clinic, Meditation can give a person a sense of calm, peace and balance that benefits both their emotional well-being and their overall health. Meditation can help carry a person more calmly through their day and may improve certain medical conditions. The emotional benefits of meditation can include: Gaining a new perspective on stressful situations, Building skills to manage stress, increasing self-awareness, Focusing on the present, and reducing negative emotions. Some research also suggests that meditation may help people manage symptoms of conditions such as: Anxiety disorders, Asthma, Cancer, Depression, Heart disease, High blood pressure, Pain, Sleep problems.

The breathing tube device can serve as a bridge to make meditation more accessible and realistic to more people because it's easier to learn and practice. Subsequently, meditation has been known to expand consciousness in higher realms. Attention to breath and expanded exhalations are potential building blocks to reach this higher consciousness.

Yoga Accessory: The device can also be used to support the practice of Yoga. The role of breath is very important in the practice of Asanas or Yoga positions or yoga postures. First it is needed to understand why breathing is incorporated in yoga practice. The breath is Prana or vital force. A person's body requirements of oxygen or pranic energy are changing depending on their actions.

Reminder to be mindful and present: The breathing tube device is also configured to serve as a reminder to a user to return to their breath and be present. By wearing the accessory as a necklace, bracelet, ring, or key chain broaden use and/or not limited to; the breathing tube device acts as a keepsake that prompts a user to be mindful in every moment. Even when the breathing tube is not technically in use (manifesting longer exhales) it can boost mindfulness and attention to the users breath by merely glancing at it.

Mindfulness is about cultivating, as the Buddhist teacher Joseph Goldstein has written, "the quality and power of mind that is aware of what is happening, without judgement and without interference." Mindfulness is, however, a specialty of Buddhism. As Goldstein also notes, the Buddha himself referred to it as "the path to enlightenment." The Four Foundations of Mindfulness are key things that we should practice being mindful of. These are: our bodies, our feelings, our minds themselves, and phenomena/the world around us. By training in mindfulness of these four foundations, we see, more and more, how all of these things really are, outside from our conceptual ideas of them.

The breathing tube device synergizes with mindfulness in that both practices were born from Buddhism and designed to make people aware, present, and at peace in their minds. The Breathing Tube Device was specifically inspired by the Komusō Monks who were a group of Japanese monks of the Fuke school of Zen Buddhism who flourished during the Edo period of 1600-1868. Komusō Monks were characterized by a straw bascinet worn on the head, manifesting the absence of specific ego. They were also known for playing solo pieces on the Shakuhachi (a type of Japanese bamboo flute). These pieces were played during a meditative practice called as a method of attaining enlightenment, and as a healing modality.

Komusō practiced suizen, which is meditation through the meditative blowing of a Shakuhachi. Literally meaning "blowing Zen", suizen pieces prioritized precise breathing control as a function of Zen mindfulness and many were designed to be played in time with a monk's footsteps as he marched long distances on pilgrimage.

The flute that the Komusō monks played to meditate, called the Shakuhachi, inspired the creation and design of the breathing tube device in that the instrument shaped exhalations to stimulate peace of mind. Modern day culture may not support the tradition of walking the streets with a basket on your head playing a meditational flute so the inventor of the device transformed the ancient practice into a small keepsake which functions to remind a user to be mindful and breathe Zen.

Fashionable Accessory: The breathing tube device was also designed to be noticed as a beautiful keepsake to symbolize a personal relationship or affiliation with meditation, mindfulness, Buddhism, Yoga, Zen, deep breathing, and/or simply peace of mind. The Breathing Tube Device can be associated or recognized universally as jewelry in the form of a necklace, bracelet, ring, earing, belt buckle, hair utensil, key chain, or loose attachment or as any type of accessory. The device is the first of its kind in that offers the user beauty, representation, and a utility for breathing.

There are other accessories available on the open market offering beauty and representation but none that are specifically designed to help guide exhalations. The breathing tube device is the first multidimensional tool that acts as a piece of jewelry and a utility for breathe. Users can wear the device for the beauty, representation, utility, or all.

Breathing Tube Device Engineering: The breathing tube device was designed as an instrument through which human exhalations can be extended to provide comfort as it relates to relieving stress and cultivating peace of mind. The size of the actual hole through the tube and length of the tube was engineered to lengthen exhalations and was designed for this exact purpose. The specifications of the example device length and size were determined based on exhalation testing which revealed the ideal tube construction as detailed in the illustrations supplied in this application. Since everyone requires or prefers a different exhalation time to reach ideal breathing rates, the device serves to guide the user to their personal preference of exhalation time consistent with feeling good. The device may be manufactured using a CAD design to measure exact specifications and then developed into a mold from which the tube may be cast although any other suitable construction method may be utilized. From there the device can be made using many different materials as some of which are detailed below.

In some embodiments, the breathing tube device can comprise an elongated body which may be cylindrical in shape. The body can be hollow (chamber) so as to form the general shape of a tube. The tube may comprise a first end (bottom) and a second end (top). The user may interact with the device by placing their mouth in communication with the first end so that the user may exhale through their mouth into and through the hollow body (chamber) of the device. In further embodiments, the top end can comprise a connective part (such as a bail) which can be configured to be coupled to one or more objects such as clothing, strings, necklaces and chains, bracelets, headbands and hair accessories, and the like. In the example shown in the Figs., the connective part can comprise a loop of material, such as which can be used to form the body, that may be coupled to the body and preferably on or proximate to the second end. In alternative embodiments, the device can comprise one or more connective parts which may be coupled or removably coupled anywhere to the body and which can comprise any type of fastener such as a clip, clasp, carabineer, pin, or any other type of fastening method which can be configured to secure the device to one or more objects such as clothing, strings, necklaces and chains, bracelets, headbands and hair accessories, and the like.

Breathing Tube Device Materials: The breathing tube device preferably can be manufactured using a brass base with different options of metal plating including rose gold, silver, hematite, and copper. The breathing tube device can also be manufactured using many different materials including but not limited to: different variations of wood, plastic, metals (gold, rose gold, silver, rhodium, pure platinum, copper, brass, and hematite), plated metals, plated wood, stone, concrete, acrylic, and rubber. The plated materials can be sandblasted or washed to provide a more vintage appearance.

Breathing Tube Device Mechanics: The user can insert the opening 6 of the tube 3 into their mouth. The user just needs to insert the opening 6 of the device into their mouth and secure it with their lips like a whistle or straw. The user should insert the opening 6 as labeled on the drawing into their mouth, not exit 7. The reason for this is because the exit 7 includes a connective part 1 that could restrict the exhalation.

The user is recommended to deeply inhale through their nose, not mouth. The user should inhale through the nose for several reasons although this is not required to receive the full benefits of the breathing tube 3 device. Air inhaled through the nose is warmed and moistened, so it does not irritate the sensitive airways. Air inhaled through the nose is also filtered, (spun as it rushes round specially designed structures the concha or turbinates, so any particles—allergens, microbes—stick to the mucus lining of the airways where they are destroyed by enzymes and gases with antimicrobial properties). Finally, inhaling through the nose can help to slow the pace of the user's breath so they can begin to develop a slower rhythm of breath and become more aware, relaxed, and present. The amount of time taken to inhale can range as it is dependent on the comfort levels of the user.

The user should exhale through their mouth into the breathing tube 3 device releasing a full exhalation, as long as it is comfortable for them. This is the most important step as the breathing tube device 3 is configured to slow exhalation through the mouth. The time of the exhalation can range and is completely dependent upon the user as everyone's physical biology is different, especially as it relates to lung health, age, physical fitness, bronchial clarity, and prior experience with deep breathing.

The user is recommended to repeat these steps as many times as necessary to reach their intended comfort levels. Sometimes one breath is all that is necessary to help the user either feel better or reset their breath. Others may find it necessary to use the device for more than three breathes. The user is encouraged to listen to their body and start to develop a sense for what pace of breath is right for them.

FIGS. 8-10 illustrate another embodiment in which the air flow through the device is adjustable. Exit Hole Vent Cap featured in FIG. 8-10 is a removable piece that can be fitted over the exit 7 of the breathing tube device. FIG. 8 is the bottom view of the cap with slanted vent spokes 9. Reference No. 10 is space for the air to pass through and 8 is the wall side of the cap that fits around (over) the walls of the device 7. FIG. 9 is the top view of the cap with a flat top 11. FIG. 10 is the side view with outer wall 12.

The Exit Hole Vent Cap is designed to govern the flow of air through the breathing device chamber 3 to regulate the desired air flow of the exhalation. These caps are equipped with angled vent spokes 9 that limit air flow. For example, the caps can contain 2-7 vent spokes 9 that the user can select from to decide which vent cap delivers their ideal exhalation. These caps can be made from (but not limited to) metal, copper, brass, plastic, rubber, silicon, acrylic, and wood. The caps can be made to attach to any size of chamber exit (7) from 2 to 10 millimeters. This example is only one way of adjusting the air flow through the device. Any desired means of adjusting the air flow through the device can be utilized as desired.

While the claimed invention has been described in detail and with reference to specific embodiments thereof, it will be apparent to one of ordinary skill in the art that various changes and modifications can be made to the claimed invention without departing from the spirit and scope thereof.

The invention claimed is:

1. A breathing device in a form of jewelry consisting essentially of:
   an elongated tube having a length of 30 to 75 millimeters from a first end to a second end defining a central chamber having a uniform diameter of 3 to 6 millimeters throughout the length of the elongated tube;
   an opening on the first end of the elongated tube constructed to be inserted into a user's mouth; an exit on the second end of the elongated tube; and
   a securing structure connected to the elongated tube, the securing structure comprises a necklace or bracelet is configured to secure the elongated tube on the user as jewelry,
   wherein the length and the diameter of the elongated tube are being constructed to restrict an exhaled breath of a user to slow breathing of the user to a desired breathing rate.

2. The breathing device according to claim 1, further comprising a bail connected to the elongated tube constructed to mount the elongated tube to the securing structure.

3. The breathing device according to claim 1, further comprising an angled surface at the first end of the elongated tube.

4. The breathing device according to claim 1, wherein the elongated tube has a round, oval, square, polygonal, or irregular shape.

5. The breathing device according to claim 1, wherein an air flow rate through the device is adjustable by the user.

6. The breathing device according to claim 1, further comprising a removable end cap that restricts air flow there through.

7. The breathing device according to claim 1, wherein the diameter of the central chamber through the elongated tube has been engineered to lengthen exhalations of the user.

8. A method of slowing a user's breathing rate and wearing a breathing device as jewelry comprising:
   providing the breathing device comprising an elongated tube having a length of 30 to 75 millimeters from a first end to a second end defining a central chamber having a diameter of 3 to 6 millimeters throughout the length of the elongated tube,
   an opening on the first end of the elongated tube configured to be inserted into a user's mouth,
   an exit on the second end of the elongated tube, and
   a securing structure connected to the elongated tube, wherein the length and the diameter of the elongated tube are being constructed to restrict an exhaled breath of a user to slow breathing of the user to a desired rate, and
   the securing structure comprises a necklace or bracelet configured to secure the elongated tube on the user as jewelry;
   wearing the breathing device as jewelry by the user;
   inserting the first end of the elongated tube into a user's mouth; and exhaling by the user through the opening, the central chamber and the exit by the user to slow the user's breathing rate.

9. The method according to claim 8, further comprising an angled surface at the first end of the elongated tube.

10. The method according to claim 8, wherein the elongated tube has a round, oval, square, polygonal, or irregular shape.

11. The method according to claim 8, wherein the air flow rate through the breathing device is adjustable by the user.

12. The method according to claim 8, further comprising a removable end cap that restricts air flow there through.

13. The method according to claim 8, wherein exhaling by the user through the opening, the central chamber and the exit lengthens and slows a rhythm of the user's breathing.

14. The method according to claim 8, wherein exhaling by the user through the opening, the central chamber and the exit reduces anxiety or stress in the user.

15. The method according to claim 8, wherein exhaling by the user through the opening, the central chamber and the exit provides a shift to calm in the user.

16. The method according to claim 8, wherein exhaling by the user through the opening, the central chamber and the exit introduces and teaches breathing aspects of meditation and yoga.

17. The method according to claim 8, wherein exhaling by the user through the opening, the central chamber and the exit activates the parasympathetic nervous system to initiate deeper and more meaningful exhalations, heart rate, blood pressure, and muscular tension each lower which allows the user to enter a more still and relaxed state.

18. The method according to claim 8, wherein exhaling by the user through the opening, the central chamber and the exit sets a pace of breath of a user by extending the exhalation which sets the user's state of mind and reverses the negative effects of stress or prevents stress by committing to a calm pace of breath and calm state of mind.

19. The method according to claim 8, wherein exhaling by the user through the opening, the central chamber and the exit until anxiety or increased heart rate abates.

20. The method according to claim 8, wherein exhaling by the user through the opening, the central chamber and the exit removes the frustration of pacing the user's breath because focusing by the user on the breathing device turns the user's attention specifically to the user's breath and away from distractions.

21. The method according to claim 8, wherein the diameter of the central chamber through the elongated tube has been engineered to lengthen exhalations of the user.

* * * * *